United States Patent [19]

Comins et al.

[11] Patent Number: 5,262,571
[45] Date of Patent: Nov. 16, 1993

[54] CYCLOALKYL-BASED CHIRAL AUXILIARIES AND METHOD MAKING THE SAME

[75] Inventors: Daniel L. Comins, Cary; James M. Salvador, Raleigh, both of N.C.

[73] Assignee: North Carolina State University, Raleigh, N.C.

[21] Appl. No.: 855,721

[22] Filed: Mar. 20, 1992

[51] Int. Cl.[5] .......................................... C07C 29/159
[52] U.S. Cl. .................................. 568/807; 568/810; 568/821; 568/828; 568/834; 568/838; 435/280
[58] Field of Search .............. 568/807, 810, 828, 821; 568/834, 838; 435/280

[56] References Cited

U.S. PATENT DOCUMENTS 3,109,018 10/1963 Hanover ............................... 260/475
3,607,651 9/1971 Moroz .................................. 195/30
3,943,181 3/1976 Fleischer et al. ..................... 260/631 R (List continued on next page.)

FOREIGN PATENT DOCUMENTS 52-51095 6/1977 Japan.
54-101487 8/1979 Japan.
1-235599 2/1989 Japan.

OTHER PUBLICATIONS

Carey & Sundberg; *Adv. Org. Chem.*, 2nd ed., Part B: Rxns & Syn; 1984, pp. 498–506.

(List continued on next page.)

*Primary Examiner*—Marianne M. Cintins
*Assistant Examiner*—Michael B. Hydorn
*Attorney, Agent, or Firm*—Bell, Seltzer, Park & Gibson

[57] ABSTRACT

A process of synthesizing enantiomerically pure compounds defined by Formula V,

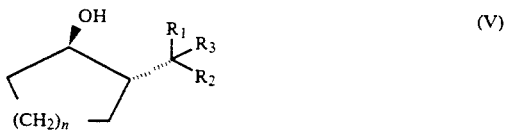

which are useful as chiral auxiliaries is disclosed. The process comprises, first, combining a base of Formula $Y^-Z^+$ (Formula I), wherein $Y^-$ is an organic anion and $Z^+$ is an inorganic cation, with a compound of Formula II,

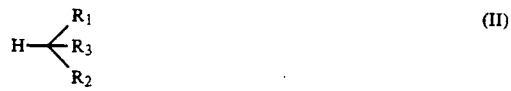

wherein $R_1$ is a $C_1$–$C_4$ alkyl group and $R_2$ is the same as $R_1$, or wherein $R_1$ and $R_2$ together form cyclopentane or cyclohexane, and wherein $R_3$ is a substituted or unsubstituted aryl group, to form a compound defined by Formula III,

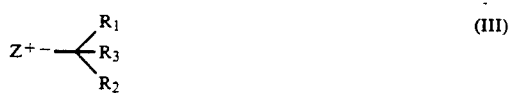

then:
(b) reacting the compound of Formula III with a cyclic epoxide defined by Formula IV,

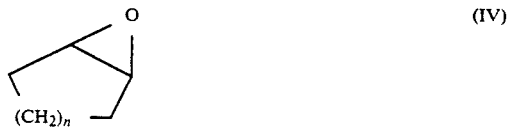

wherein n is 1, 2, or 3, to form a racemic mixture of a compound defined by Formula V.

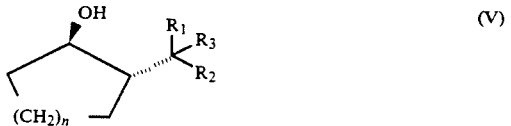

In a preferred embodiment, the method further comprises stereospecifically esterifying one of the enantiomers of the racemic mixture of compound (V) and a carboxylic acid with an enzyme in an organic solvent, wherein said acid is a $C_2$–$C_{20}$ alkyl acid, benzoic acid or a $C_2$–$C_{14}$ alkyl benzoic acid, and then separating the esterified enantiomer from the non-esterified enantiomer.

15 Claims, No Drawings

U.S. PATENT DOCUMENTS

| | | | |
|---|---|---|---|
| 4,418,225 | 11/1983 | House | 568/829 |
| 4,720,558 | 1/1988 | Kaulen | 549/443 |
| 4,916,074 | 4/1990 | Yoshida et al. | 435/280 |
| 4,962,031 | 10/1990 | Yoshida et al. | 435/280 |
| 4,963,492 | 10/1990 | Keller et al. | 435/280 |
| 4,996,158 | 2/1991 | Oda et al. | 435/280 |
| 5,021,345 | 6/1991 | Urban et al. | 435/180 |
| 5,032,523 | 7/1991 | Amano et al. | 435/280 |
| 5,057,427 | 10/1991 | Wald et al. | 435/280 |

OTHER PUBLICATIONS

Okumura et al; Biochimica et Biophysica Acta, 575 (1979); pp. 156–165.

R. Lawrence, "The Resolution and Use of Chiral Auxiliaries in Asymmetric Synthesis," Dissertation presented to the faculty of the University of Texas at Austin (UMI, Ann Arbor, Mich.) Dec. 1988.

R. Benkeser et al., *J. Am. Chem. Soc.* 85, 3984–3989 (1963).

G. Langrand et al., *Tetrahedron Letters*, 26, No. 15, 1857–1860 (1985).

W. Oppolzer et al., *Helvetica Chimica Acta* 63, Fasc. 7, 2015–2018 (1980).

J. Whitesell, *Acc. Chem. Res.* 18, 280–284 (1985).

J. Whitesell and R. Lawrence, *CHIMIA* 40, No. 9, 318–322 (1986).

D. Wilhelm et al., *J. Am. Chem. Soc.* 106, No. 2, 361–367 (1984).

CYCLOALKYL-BASED CHIRAL AUXILIARIES AND METHOD MAKING THE SAME

FIELD OF THE INVENTION

This invention relates generally to the synthesis of chiral molecules, and more particularly relates to a process for synthesizing trans-2-substituted cyclic hydrocarbon alcohols.

BACKGROUND OF THE INVENTION

The importance of chiral, nonracemic structural units in a number of biologically active compounds has led to intensive efforts to develop efficient syntheses for these compounds. Chiral auxiliary mediated asymmetric synthesis has played an important role in the development of a range of chemical transformations that can be carried out with the high degree of absolute stereocontrol necessary for effective assemblage of biologically important compounds.

Enantiopure (−)-8-phenylmenthol (Formula VII)

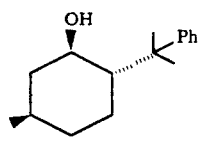

is a highly efficient chiral auxiliary which has been demonstrated to have powerful stereochemical directing influences in several types of synthetically useful reactions. See generally Oppolzer et al., *Helv. Chim. Acta* 63:2015 (1980); see also Whitesell, *Acc. Chem. Res.* 18:280 (1985). This chiral auxiliary is commercially available but expensive. Alternatively, the compound can be prepared from (+)-pulegone in five synthetic steps. Both the cost of the compound and its lengthy synthesis restrict its industrial use. Furthermore, the enantiomer of the compound of Formula (VII), (+)-8-phenylmenthol, is very expensive and requires a complicated synthesis with many steps.

Accordingly, there is a clear need for inexpensive, readily available chiral compounds. There is a similar need for the enantiomers of such compounds. Finally, there is a need for a relatively simple process to make and separate such enantiomers.

SUMMARY OF THE INVENTION

In view of the foregoing, a first object of the present invention is to provide a process for expediently and inexpensively producing useful chiral auxiliaries.

A second object of the invention is to provide a process for resolving the optical enantiomers of a racemic mixture of useful chiral auxiliaries.

An additional object of the invention is to provide new compounds useful in industrial, chemical, and biochemical processes as chiral auxiliaries.

These and other objects are met by the present invention. The invention comprises a process for synthesizing useful chiral auxiliaries comprising the steps of combining a base of Formula I, $$Y^- Z^+ \qquad (I)$$

wherein $Y^-$ is an organic anion and $Z^+$ is an organic cation, with a compound of Formula II,

wherein $R_1$ is a $C_1$–$C_4$ alkyl group and $R_2$ is the same substituent as $R_1$, or wherein $R_1$ and $R_2$ together form cyclopentane or cyclohexane, and wherein $R_3$ is an unsubstituted aryl group or a substituted aryl group containing substituents which are weaker Bronsted acids than the hydrogen atom of formula II to form a compound defined by Formula III,

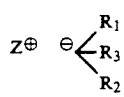

then reacting with the compound of Formula III a cyclic epoxide defined by Formula IV,

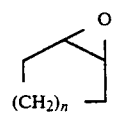

wherein n is 1, 2, or 3, to form a racemic mixture of a compound defined by Formula V.

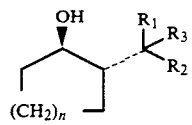

This racemic mixture can then be optically resolved to produce its optically pure enantiomers for use in other processes.

A second aspect of the invention is a compound of the general formula VI

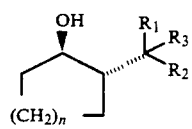

wherein n is 1, 2, or 3, $R_1$ is a $C_1$–$C_4$ alkyl group and $R_2$ is the same as $R_1$, or wherein $R_1$ and $R_2$ together form cyclopentane or cyclohexane, and $R_3$ is benzene substituted 1 to 5 times with $C_3$–$C_7$ secondary alkyl groups, or $C_4$–$C_7$ tertiary alkyl groups, or $R_3$ is selected from the group consisting of naphthalene, optionally substituted 1 to 5 times with $C_3$–$C_7$ secondary alkyl groups or $C_4$–$C_7$ tertiary alkyl groups. These compounds are useful as chiral auxiliaries.

DETAILED DESCRIPTION OF THE INVENTION

The present invention includes a process for synthesizing useful chiral auxiliaries. The process comprises the steps of combining a base of Formula I,

wherein $Y^-$ is an organic anion and $Z^+$ is an inorganic cation, with a compound of Formula II,

wherein $R_1$ is a $C_1$-$C_4$ alkyl group and $R_2$ is the same substituent as $R_1$, or wherein $R_1$ and $R_2$ together form cyclopentane or cyclohexane, and wherein $R_3$ is an unsubstituted aryl group or a substituted aryl group containing substituents are weaker Bronsted acids than the hydrogen atom of Formula II to form a compound defined by Formula III,

then reacting with the compound of Formula III a cyclic epoxide defined by Formula IV,

wherein n is 1, 2, or 3, to form a racemic mixture of a compound defined by Formula V.

The enantiomers of compound of Formula V can then be stereospecifically resolved for use in processes that require an enantiomeric form.

Turning first to the combining step, the base of Formula I comprises a anion-cation pair denoted by $Y^-Z^+$. This base must be sufficient in strength to remove the hydrogen atom illustrated in Formula II. Exemplary cations ($Z^+$) include Group I metals, such as lithium, potassium, and sodium, and complexes of Group II metals and halogens, such as magnesium chloride and zinc chloride. Preferred cations are lithium and potassium, with potassium being more preferred. Exemplary anions ($Y^-$) include $C_1$-$C_6$ alkyl anions and tri-alkyl substituted silicon methyl anions. Preferred anions are butane anion and trimethyl silicon methyl anion, with butane being more preferred. The most preferred anion-cation pair is butyl potassium.

The compound of Formula II comprises alkyl groups $R_1$ and $R_2$ and aryl group $R_3$. As used herein, the term "aryl" includes any of the group of unsaturated cyclic hydrocarbons, typified by benzene, having a stable electron shell configuration, and any heterocyclic ring compounds having a similarly stable electron shell configuration. The presence of the aryl group in $R_3$ permits the deprotonation of the hydrogen illustrated in Formula II because the ring structure of the aryl group is able to distribute the negative charge of the electron pair remaining after deprotonation and thus can stabilize the resulting anion molecule. $R_3$ can be any substituted or unsubstituted aromatic group which is capable of stabilizing the anion after deprotonation. Exemplary aryl groups include benzene, naphthalene, anthracene, phenanthrene, indene, phenalene, biphenyl, furan, thiophene, thiaindine, thianthrene, isobenzofuran, pyridine, pyrazole, pyrazine, pyrrole, imidazole, pyrimidine, pyridazine, indolazine, isoindole, indole, indazole, purine, quinoline, isoquinoline, phthalazine, quinoxaline, quinazoline, ciinoline, pteridine, carbazole, β-carbolene, phenazine, furazan, and isothiazole.

The aryl group of Formula II can be unsubstituted or substituted with one to five substituents. Suitable substituents are those which are weaker Bronsted acids than the hydrogen illustrated in Formula II and therefore are less susceptible to deprotonation. Exemplary suitable substituents are secondary $C_3$-$C_7$ alkyl groups, tertiary $C_4$-$C_7$ alkyl groups, tertiary $C_1$-$C_3$ alkyl amines, benzyl groups optionally substituted from 1 to 5 times with $C_1$-$C_4$ alkyl groups, $C_1$-$C_4$ alkoxy groups, alkyl ethers, and phenyl ethers. Preferably, $R_3$ is benzene, naphthalene, phenantrene or anthracene optionally substituted 1 to 5 times with secondary $C_3$-$C_7$ alkyl groups or tertiary $C_4$-$C_7$ alkyl groups.

Compounds unsuitable for substitution on an aryl or benzyl group of $R_3$ include those compounds which are more susceptible to deprotonation than the hydrogen atom illustrated in Formula II. Exemplary unsuitable substituents include primary alkyl groups, nitro groups, carboxyl groups, ketones, aldehydes, primary amines, secondary amines, unsaturated alkenes, and alkyl sulfides.

In choosing $R_1$ and $R_2$, two requirements must be met. First, the tertiary carbon atom to which they bond must be achiral; thus, either $R_1$ and $R_2$ must be the same substituent, or they together must form a cyclic substituent, such as cyclopentane or cyclohexane, so that the tertiary carbon retains its achiral character. Second, $R_1$ and $R_2$ must be sufficiently stable that they do not deprotonate in the presence of the base of Formula I. Exemplary for $R_1$ and $R_2$ if they are to be the same substituent are $C_1$-$C_4$ alkyl groups, with methyl or ethyl groups being preferred. If $R_1$ and $R_2$ are to combine to form a cyclic substituent, cyclopentane and cyclohexane are preferred.

The reaction of the combining step can be produced by a variety of methods. See e.g., Benkeser et al., *J.Am. Chem. Soc.* 85:3984 (1963), and Wilhelm et al., *J. Am. Chem. Soc.* 106:361 (1984), which describe a method for producing α-cumyl potassium. The reaction should be carried out in an aprotic organic solvent, which is preferably non-polar. Preferred solvents are hexane, cyclohexane, and mixtures thereof, with hexane/cyclohexane mixtures being more preferred. The temperature of the reaction vessel can be maintained at between about $-25°$ C. and $75°$ C., with a range of $10°$ C. to $50°$ C. being preferred. It is desirable to carry out the reaction in the same reaction vessel to be used to carry out the subsequent substitution step.

The cyclic epoxide of Formula IV can be any cyclic hydrocarbon having an epoxide group that will react with the compound of Formula III to produce the desired racemic cyclic alcohol product of Formula V. The cyclic epoxide is exemplified by cyclopentene oxide, cyclohexene oxide, and cycloheptene oxide, with cyclohexene oxide being more preferred.

The reaction of the compounds of Formula III and Formula IV preferably is carried out in situ, i.e., in the same reaction vessel as was used to synthesize the compound of Formula III. The temperature of the reaction can be between −25° C. and 75° C., with a range of 20° C. to 40° C. being preferred. The reaction should be carried out in an organic solvent. An aprotic, non-polar solvent is preferred; exemplary non-polar aprotic solvents are hexane and cyclohexane, with hexane/cyclohexane mixtures being preferred.

The enantiomers that comprise the racemic mixture of compound V can be resolved by stereospecifically esterifying one enantiomer of the racemate and a carboxylic acid with an enzyme in an organic solvent, then separating the esterified fraction from the non-esterifed enantiomer. After separation, the non-esterified enantiomer is then available for use in reactions that require an enantiomerically pure reactant.

The carboxylic acid used in the esterification can be any carboxylic acid that will, in combination with the enzyme, stereospecifically esterify one enantiomer of the racemic mixture while not reacting with the other enantiomer. It is desirable in choosing the carboxylic acid to compare the boiling point of the ester to be formed with that of the non-esterified enantiomer; separation is simpler and more direct if the boiling points for these compounds vary significantly. Exemplary acids include $C_2$–$C_{20}$ acids, benzoic acid, and benzyl $C_2$–$C_{14}$ alkyl acids. Preferred acids are $C_8$–$C_{14}$ fatty acids or acids that have at least one benzyl group. More preferred are lauric acid, caprylic acid, and capric acid.

The enzyme used in the esterification can be any enzyme that will stereospecifically esterify the chosen carboxylic acid with one of the enantiomers of Formula V. If a fatty acid is used as the esterfying carboxylic acid, a lipase is a preferred enzyme. It is desirable to select an enzyme with a high reaction rate to decrease the time needed for reaction. It is also desirable to select an enzyme that will not be degraded or denatured by the presence of the other reactants so that it can be recovered and reused.

Suitable solvents for the reaction are organic solvents which will not interfere with the esterification. Aprotic, nonpolar solvents are preferred. It has been seen that the choice of solvent can affect the esterification rate. To this end, hexane and cyclohexane are more preferred solvents, with cyclohexane being a more particularly preferred solvent.

The reaction can be carried out at between 0° C. and 75° C., with a range of 30° C. to 50° C. being preferred. The reaction can last from 12 hours to 7 days depending on the choice of enzyme, solvent, and compound to be resolved. It has been seen that yield and optical purity improve if the reaction is conducted in multiple cycles; i.e., esterifying a portion of the racemic mixture, removing the esterified portion, and repeating the reaction on the unreacted portion of the mixture. Once a desired percentage of one enantiomer has been esterified, the non-esterified enantiomer can be separated from the solvent and remaining enzyme by methods known to those in this art such as distillation or filtration.

The esterified enantiomer can be hydrolyzed to produce the optical isomer to that described above. Any hydrolysis method known in the art can be used to cleave the ester bond. Refluxing the ester in alcohol solvent containing an aqueous base is preferred.

The present invention also provides compounds useful as chiral auxiliaries in a number of industrial, chemical, and biochemical processes. The compounds are defined by Formula VI

wherein n is 1, 2, or 3, $R_1$ is a $C_1$–$C_4$ alkyl group and $R_2$ is the same as $R_1$, or wherein $R_1$ and $R_2$ together form cyclopentane or cyclohexane, and $R_3$ is either benzene substituted 1 to 5 times with $C_3$–$C_7$ secondary alkyl groups, or $C_4$–$C_7$ tertiary alkyl groups, or $R_3$ is selected from the group consisting of naphthalene, anthrecene, phenanthrene, and biphenyl optionally substituted 1 to 5 times with $C_3$–$C_7$ secondary alkyl groups or $C_4$–$C_7$ tertiary alkyl groups. Preferably, $R_1$ and $R_2$ are either methyl or ethyl. Preferably $R_3$ is benzene substituted 1 to 2 times at the 3, 4, and 5 positions with secondary $C_3$–$C_7$ alkyl groups or tertiary $C_4$–$C_7$ alkyl groups, naphthalene, anthracene, or biphenyl. More preferably, $R_3$ is benzene substituted at at least one of its 3, 4, or 5 positions with isopropyl groups or t-butyl groups, naphthalene, or biphenyl. Preferably n is 2.

The present invention and its advantages over the prior art will be more fully understood and appreciated from the illustrative examples that follow. It is to be understood that the examples are for the purpose of illustration and are not intended to be limiting upon the scope of the invention. A person skilled in the applicable arts will appreciate from these examples that the invention can be embodied in many different forms other than those specifically disclosed.

As used herein, "L" means liters, "mL" means milliliters, "mol" means moles, "mmol" means millimoles, "C" means degrees Centigrade, "M" means molar concentration, "mm Hg" means millimeters of mercury, "g" means grams, "Hz" means Hertz, and "U/g" means specific enzymatic activity per gram of enzyme.

EXAMPLE 1

Preparation of racemic trans-2-(1-methyl-1-phenylethyl)cyclohexanol (trans-2-cumylcyclohexanol)

The procedure is begun with the production of α-cumylpotassium by the method first described in Benkeser et al., *J. Am. Chem. Soc.* 85:3984 (1963), and elaborated in Wilhelm et al., *J. Am. Chem. Soc.* 106:361 (1984). An oven-dried 3 liter three-necked, round-bottomed flask equipped with a 250 mL graduated addition funnel, a mechanical stirrer and a gas inlet was purged with argon while hot. After the flask had cooled, 925 mL (1.1 mol) of 18% by weight potassium t-amylate in cyclohexane (available from Callery Chemical Company, Callery, Pa., U.S.A.) and 555 mL (4.0 mol) of freshly distilled cumene having a boiling point of 152°–155° C. were mixed within to produce a light amber solution. The reaction flask was placed in a circulating water bath held at 25° C. Next, 485 mL (1.0 mol) of 2.06 M n-butyllithium in hexane (available from Alfa Products, Ward Hill, Mass., U.S.A.) was added dropwise to the flask over a 2 hour period during which the water bath temperature was not permitted to rise above 30° C. As n-butyllithium was added, the reaction mixture changed from a bright red solution to a dark purple suspension. The water bath was removed after the addition was completed. The suspension was stirred for two days using the mechanical stirrer, after which the reaction flask was again placed in a 25° C. circulating-water bath in preparation for the addition of cyclohexene oxide.

The next step in the synthesis was the addition of cyclohexene oxide to α-cumylpotassium to produce trans-2-cumylcyclohexanol. Dropwise addition of 105 mL (1.0 mol) of cyclohexene oxide (available from Lancaster Synthesis, Ltd., Windham, N.H., U.S.A.) followed; as before, the cyclohexene oxide addition was controlled so that the bath temperature did not rise above 30° C. As cyclohexene oxide was added, the reaction mixture thinned and became black. After this addition, the mixture was stirred for 3 hours. The reaction flask was cooled in an ice bath and 750 mL of saturated aqueous ammonium chloride was added slowly to the reaction mixture, which changed in color from light brown to bright orange to light brown again; concurrently, a white precipitate that had formed during the initial stages of the addition dissolved.

To recover the product, the mixture was transferred to a separatory funnel and the aqueous layer was separated and saved. The organic layer was washed three times with 100-mL portions of water and twice with 100-mL portions of saturated aqueous sodium chloride. The aqueous layer from the first separation was combined with the wash solutions; the washes present in this solution were back extracted with three 100 mL portions of dichloromethane. The dichloromethane extracts were combined with the organic layer, dried over potassium carbonate, and decanted. Dichloromethane and excess cumene were removed by evaporation on a rotary evaporator under aspirator pressure at 90° C.

The light-green oil which remained (235 g) was distilled at 0.5 mm Hg using a Kugelrohr apparatus at 80°–120° C. to produce 213 g of a crude viscous oil. This viscous oil was dissolved in 200 mL of petroleum ether (boiling point 30°–60° C.), cooled in a freezer at −20° C., and seeded. The solution produced 189 g of off-white crystals, which quantity was 87 percent of the theoretical yield based on the cyclohexene oxide included in the reaction. This material was recrystallized from 200 mL of petroleum ether to produce 183 g of white crystals (84% of theoretical yield) of racemic trans-2-cumyl-cyclohexanol. The crystals exhibited a melting point of 49.5°–51.5° C. (45.5°–47.5° C. was reported by Whitesell et al., *Chimica* 40:318 (1986)) and the following spectral data in nuclear magnetic resonance characterization: $^1$H NMR (CDCl$_3$) 7.41 (d, 2 H, J=8.1 Hz), 7.32 (t, 2 H, J=7.7 Hz), 7.18 (t, 1 H, J=7.3), 3.50 (ddd, 1 H, J=4.4, 9.5, 14.3), 1.94–1.60 (m, 5 H), 1.43 (s, 3 H), 1.29 (s, 3 H), 1.24–1.20 (m, 3 H), 1.09–0.93 (m, 2 H); $^{13}$C NMR (CDCl$_3$) 150.9, 128.0, 125.5, 125.3, 72.9, 54.1, 39.8, 36.6, 27.4, 26.7, 26.0, 25.2, 24.8.

EXAMPLE 2

Resolution of trans-2-cumylcyclohexanol

The purpose of this reaction is to enzymatically resolve the enantiomers which comprise the racemic mixture produced by Example 1 by using a modified Triantaphylides esterification method. See Langrand et al., *Tetrahedron Lett.* 26:1857 (1985). A 218.35 g (1.0 mmol) quantity of the final product of Example 1, racemic trans-2-cumylcyclohexanol, was stirred and heated at 40° C. with 200 g (1.0 mmol) of 98 percent lauric acid in 4 L of cyclohexane. Next, 655 g (35,800 U/g, available from Amano, Troy, Va., U.S.A.) of Lipase AY 30 was added to the solution to form the laurate ester of (−)trans-2-cumylcyclohexanol. The progress of the formation of the laurate ester and the enantiomeric excess of unreacted (+)-trans-2-cumylcyclohexanol was monitored by allowing the reaction suspension to settle for five minutes, removing 1.0 μL aliquots from the supernate, and analyzing the aliquots on a Chiralcel-OJ liquid chromatography column (available from J. T. Baker, Inc., Phillipsburg, N.J., U.S.A.) using 10% isopropanol/hexanes as the solvent and eluting at 0.4 mL/min.

After 41 hours, at which point 46 percent of the (−)-trans-2-cumylcyclohexanol had esterified, the lipase was filtered off and air dried for five days. The solvent was evaporated from the filtrate and the remaining oil (437 g) was vacuum distilled bulb to bulb. This distillation produced two fractions. The first fraction, which was obtained during distillation at up to 160° C. (0.5 mm Hg), was a 225.7 g mixture of (+)-trans-2-cumylcyclohexanol (103 g), (−)-trans-2-cumylcyclohexanol (8.6 g), lauric acid (105 g), and laurate ester (9.1 g). The second fraction remained in the distillation pot and comprised 180.7 g (45%) of laurate ester.

The first fraction was resubjected to the above esterification procedure using the recovered lipase to produce a mixture of (+)-trans-2-cumylcyclohexanol, lauric acid, and laurate ester. This mixture was stirred with 138 g (1.0 mol) of potassium carbonate in 500 mL of hexanes. The precipitated potassium laurate was filtered off and washed with hexanes. The filtrate was evaporated and the residue was distilled (bp 90°–120° C./0.5 mm Hg) to produce 100.1 g of a clear oil. This product, (+)-trans-2-cumylcyclohexanol, was 98.4 percent optically pure at a yield of 46 percent (the theoretical yield for this resolution is 50%). The product also exhibited a specific optical rotation of $[[\alpha]_D^{22}+29.6°]$ in methanol in a concentration of 1.7 g/100 mL, which compares favorably to that reported in Whitesell et al., *Chimica* 40:318 (1986), of $[\alpha]_D+26.3°$ for the (+)-(1S, 2R) enantiomer of trans-2-cumylcyclohexanol.

EXAMPLE 3

Hydrolysis of Laurate Ester to produce (−) trans-2-cumylcyclohexanol

A mixture of 180.7 g of laurate ester, 56 g (0.85 mol, 85 percent by weight) of potassium hydroxide and 200 mL of 95% ethanol was refluxed for 3 hours to produce, after evaporation and distillation, 95.4 g (44% of the theoretical 50 % yield as calculated above) of (−)-trans-2-cumylcyclohexanol as a clear oil which was 92.3 percent optically pure. This product was reesterified as before with 100 g of lauric acid, recovered lipase AY30 (650 g), and 4L of cyclohexane at 40° C. for 2 days to give, as before, 148 g of laurate ester. The ester was hydrolyzed as before to give 78.3 g (36%) of (−)-trans-2-cumylcyclohexanol as a clear oil. The product was 98.2% optically pure and had a specific rotation of $[\alpha]_D^{27}-29.4°$, in methanol in a concentration of 2.0 g/100 mL, which compares favorably with the values reported by Whitesell et al. of $[[\alpha]_D-26.3°]$ for the (−)-(1R, 2S) enantiomer of trans-α-cumylcyclohexanol.

EXAMPLES 4-8

Synthesis of Additional Chiral Auxiliaries

Using procedures similar to that described in Example 1, other racemic mixtures closely related to trans-α-cumylcyclohexanol were synthesized. In these syntheses, the phenyl group of α-cumene was replaced with the aryl group indicated in the first column of Table 1. Table 1 also shows the yields and melting points of each of the racemic mixtures.

TABLE 1

| R | % yield | melting point (°C.) |
|---|---|---|
| 2-naphthalene | 55 | 70-71 |
| 4-(2-propyl)phenyl | 85 | oil |
| 4-(t-butyl)phenyl | 48 | 74.5-77 |
| 4-biphenyl | 49 | 91-92 |
| 3,5-diisopropylphenyl | 92 | oil |

It should be noted that the reactions were performed on a 0.01-0.10 mol scale, and the yield represents the yield of purified material obtained from distillation or recrystallization.

EXAMPLES 9-11

Resolution of Additional Chiral Auxiliaries

Three of the racemic mixtures produced in Examples 4-8 were resolved using the procedure described in Example 2 with the exception that the reactions were performed on a 20 mmol scale in hexane. Table 2 shows the reaction time, yield, purity, melting point (if applicable) and optical rotation of each resolved compound.

TABLE 2

| R | time (days) | yield (1S, 2R) (%) | $[\alpha]_D^{21}$ (°) | optical purity (%) | melting point (°C.) |
|---|---|---|---|---|---|
| 2-naphthalene | 4 + 2 | 46 | +12.0 | 99.4 | 71-74 |
| 4-(2-propyl)phenyl | 4 + 4 | 33 | +22.1 | 92.3 | oil |
| 4-(t-butyl)phenyl | 4 + 4 | 31 | +21.0 | 98.4 | 76-82 |

As described in Example 2, the procedure requires two esterification and separation cycles: after the first cycle, the crude alcohol and excess lauric acid are isolated by bulb-to-bulb distillation and resubjected to the enzymatic esterification. The column of Table 2 labelled "time" shows the duration for each of these cycles. The yield percentages are based on a theoretical maximum of 50 percent for this resolution. The optical purity was determined by chiral column HPLC analysis.

The foregoing examples are illustrative of the present invention, and are not to be construed as limiting thereof. The invention is defined by the following claims, with equivalents of the claims to be included therein.

That which is claimed is:

1. A process of synthesizing compounds useful as chiral auxiliaries, comprising the steps of:
   (a) combining a base of Formula I, $$Y^- Z^+ \quad (I)$$

wherein $Y^-$ is an organic alkyl or tri-alkyl substituted silicon methyl anion and $Z^+$ is an inorganic cation, with a compound of Formula II,

(II)

wherein $R_1$ is a $C_1$-$C_4$ alkyl group and $R_2$ is the same as $R_1$, or wherein $R_1$ and $R_2$ together form cyclopentane or cyclohexane, and wherein $R_3$ is an unsubstituted aryl group or substituted aryl group containing substituents which are weaker Bronsted acids than the hydrogen atom of Formula II, to form a compound defined by Formula III,

(III)

then:
   (b) reacting the compound of Formula III with a cyclic epoxide defined by Formula IV,

(IV)

wherein n is 1, 2, or 3, to form a racemic mixture of a compound defined by Formula V:

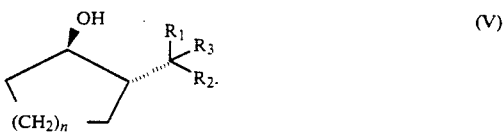

(V)

2. A process according to claim 1 wherein $R_1$ and $R_2$ are each methyl or wherein $R_1$ and $R_2$ are each ethyl.

3. A process according to claim 1 wherein n is 2.

4. A process according to claim 1 wherein $Y^-$ is butyl, and wherein $Z^+$ is potassium.

5. A process according to claim 1 wherein $R_3$ is benzene, napthalene, anthracene, and phenanthrene, $R_3$ being optionally substituted 1 to 4 times with secondary $C_3$-$C_7$ alkyl groups or tertiary $C_4$-$C_7$ alkyl groups.

6. A process according to claim 1 in which steps (a) and (b) are carried out in situ.

7. A process according to claim 1 further comprising the steps of:
   (c) stereospecifically esterifying one of the enantiomers of the racemic mixture of compound (V) and a carboxylic acid with an enzyme capable of esterifying said one enantiomer in an organic solvent, wherein said acid is a $C_2$-$C_{20}$ alkyl acid, benzoic acid or a $C_2$-$C_{14}$ alkyl benzoic acid; and
   (d) separating the esterified enantiomer from the non-esterified enantiomer.

8. A process according to claim 7 wherein the carboxylic acid is a $C_8$-$C_{14}$ fatty acid.

9. A process according to claim 7 wherein the enzyme is a lipase.

10. A process according to claim 7 wherein the organic solvent is nonpolar.

11. A process according to claim 7 further comprising:

(e) hydrolyzing the ester bond of the esterified enantiomer to recover said enantiomer.

12. A process of synthesizing compounds useful as chiral auxiliaries, comprising the steps of:

(a) combining a base of Formula I,

  (I)

wherein $Y^-$ is butyl and $Z^+$ is potassium, with a compound of Formula II,

  (II)

wherein $R_1$ is a $C_1$–$C_4$ alkyl group and $R_2$ is the same as $R_1$, or wherein $R_1$ and $R_2$ together form cyclopentane or cyclohexane, and wherein $R_3$ is an unsubstituted aryl group or subsituted aryl group containing substituents which are weaker Bronsted acids than the hydrogen atom of Formula II, to form a compound defined by Formula III,

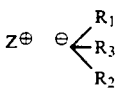  (III)

then:

(b) reacting the compound of Formula III with a cyclic epoxide defined by Formula IV,

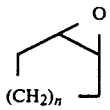  (IV)

wherein n is 1, 2, or 3, to form a racemic mixture of a compound defined by Formula V,

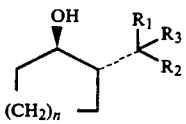  (V)

then (c) stereospecifically esterifying one of the enantiomers of the racemic mixture of compound (V) and a carboxylic acid with a lipase in a nonpolar organic solvent, wherein said acid is a $C_2$–$C_{20}$ alkyl acid, benzoic acid or a $C_2$–$C_{14}$ alkyl benzoic acid; and then (d) separating the esterified enantiomer from the non-esterified enantiomer.

13. A process according to claim 12 wherein $R_1$ and $R_2$ are each methyl or wherein $R_1$ and $R_2$ are each ethyl.

14. A process according to claim 12 wherein n is 2.

15. A process according to claim 12 wherein $R_3$ is benzene, napthalene, anthracene, and phenanthrene, $R_3$ being optionally substituted 1 to 4 times with secondary $C_3$–$C_7$ alkyl groups or tertiary $C_4$–$C_7$ alkyl groups.

* * * * *

UNITED STATES PATENT AND TRADEMARK OFFICE
CERTIFICATE OF CORRECTION

PATENT NO. : 5,262,571

DATED : 16 November 1993

INVENTOR(S) : Daniel L. Comins and James M. Salvador

It is certified that error appears in the above-identified patent and that said Letters Patent is hereby corrected as shown below:

Title page, item [54] and Column 1:

Correct Title to read "CYCLOALKYL-BASED CHIRAL AUXILIARIES AND METHOD OF MAKING THE SAME".

After BACKGROUND OF THE INVENTION insert --This invention was made with government support under Grant No. 3 R01 GM 34442 awarded by the National Institute of Health. The government has certain rights in the invention.--

Column 1, Line 67, correct "organic" to read --inorganic--.

Signed and Sealed this

Eighth Day of December, 1998

*Attest:*

*Attesting Officer*

BRUCE LEHMAN

*Commissioner of Patents and Trademarks*